(12) United States Patent
Cheng et al.

(10) Patent No.: US 10,881,819 B2
(45) Date of Patent: Jan. 5, 2021

(54) FIRST-AID MASK AND INFLATABLE STRUCTURE THEREOF

(71) Applicant: CENTER HEALTHCARE TECHNOLOGY CO., LTD., Taipei (TW)

(72) Inventors: Yung-Chu Cheng, Taipei (TW); Chien-Feng Cheng, Taipei (TW); Yu-Liang Cheng, Taipei (TW)

(73) Assignee: Center Healthcare Technology Co., Ltd., Taipei (TW)

( * ) Notice: Subject to any disclaimer, the term of this patent is extended or adjusted under 35 U.S.C. 154(b) by 580 days.

(21) Appl. No.: 15/564,821

(22) PCT Filed: Apr. 8, 2016

(86) PCT No.: PCT/CN2016/078820
§ 371 (c)(1),
(2) Date: Oct. 6, 2017

(87) PCT Pub. No.: WO2016/161965
PCT Pub. Date: Oct. 13, 2016

(65) Prior Publication Data
US 2018/0110945 A1    Apr. 26, 2018

(30) Foreign Application Priority Data

Apr. 8, 2015 (CN) .......................... 2015 1 0161744

(51) Int. Cl.
| A41D 13/11 | (2006.01) |
| A61M 16/00 | (2006.01) |
| A61M 16/06 | (2006.01) |
| A61M 16/04 | (2006.01) |
| A62B 18/10 | (2006.01) |
| A61M 21/00 | (2006.01) |
| A61M 16/10 | (2006.01) |

(52) U.S. Cl.
CPC ......... *A61M 16/0048* (2013.01); *A41D 13/11* (2013.01); *A61M 16/0493* (2014.02);
(Continued)

(58) Field of Classification Search
CPC ......... A62B 18/08; A62B 18/00; A62B 18/02; A62B 23/02; A62B 9/04; A62B 23/025;
(Continued)

(56) References Cited

U.S. PATENT DOCUMENTS 5,649,532 A * 7/1997 Griffiths ................. A62B 18/04
128/201.23
5,676,133 A * 10/1997 Hickle .................. A61M 16/00
128/202.27
(Continued)

FOREIGN PATENT DOCUMENTS

CN    202376580 U    8/2012
CN    203790402 U    8/2014
(Continued)

*Primary Examiner* — Ophelia A Hawthorne
(74) *Attorney, Agent, or Firm* — Muncy, Geissler, Olds & Lowe, P.C.

(57) ABSTRACT

The present invention relates to a mask and an inflatable structure thereof. The inflatable structure which is provided in a mask's body comprises: a ventilation seat; a sleeving connection which is sleeved at one end of the ventilation seat and sandwiches the mask's body together with the ventilation seat, with the sleeving connection provided with a socket tube so that the mask's body, the ventilation seat and the socket tube are in air communication; an air-sealed hood which is connected to the sleeving connection and provided around the socket tube. By virtue of the structure in the present invention, the air flow can be effectively imported into the patient to significantly increase the survival rate of the patient.

11 Claims, 10 Drawing Sheets

(52) U.S. Cl.
CPC ............. *A61M 16/06* (2013.01); *A62B 18/10* (2013.01); *A41D 13/1115* (2013.01); *A41D 2500/20* (2013.01); *A61M 16/0683* (2013.01); *A61M 16/1055* (2013.01); *A61M 2021/0016* (2013.01); *A61M 2205/11* (2013.01); *A61M 2205/7518* (2013.01); *A61M 2210/0662* (2013.01)

(58) Field of Classification Search
CPC ... A62B 18/025; A62B 13/11; A41D 13/1146; A41D 13/1161; A41D 13/1184; A41D 13/1192; A41D 13/11
See application file for complete search history.

(56) References Cited

U.S. PATENT DOCUMENTS

| | | | | |
|---|---|---|---|---|
| 5,735,265 | A | * | 4/1998 | Flynn ................ A61M 16/0048 128/202.28 |
| 6,691,703 | B2 | * | 2/2004 | McKinney ........ A61M 16/0048 128/202.28 |
| 2014/0196321 | A1 | * | 7/2014 | Wu .......................... A43B 7/12 36/3 B |

FOREIGN PATENT DOCUMENTS

| | | |
|---|---|---|
| CN | 204208147 U | 3/2015 |
| CN | 104759013 A | 7/2015 |
| CN | 204563231 U | 8/2015 |

\* cited by examiner

ABSTRACT# FIRST-AID MASK AND INFLATABLE STRUCTURE THEREOF

BACKGROUND OF THE INVENTION

1. Technical Field

The present invention relates to a mask and an inflatable structure thereof, and more specifically, to a first-aid mask and an inflatable structure thereof.

2. Description of Related Art

In recent years, with the frequent occurrence of incidents, such as heart disease, respiratory emergency, drowning, electric shock, drug overdose, foreign matter choking or carbon monoxide poisoning, many patients lost their precious lives in just a few minutes, due to lack of real-time rescue by the surrounding people. In case of the above situation, all patients with respiratory or cardiac arrest should be given cardiopulmonary resuscitation (CPR) immediately for first aid.

Usually in case of a brain in hypoxia for four to ten minutes, the brain cells will begin to be damaged, and the brain cells cannot be restored if the hypoxia lasts for more than ten minutes, so CPR refers to the use of chest compression and artificial respiration for keeping the blood supply of the heart, lung and brain and other vital organs of the human body.

In the process of artificial respiration, the rescuers may feel scared or retreat because of embarrassment or emesis of patients, or because they worry about whether the patients have other diseases such as infectious diseases. Some patients are even trapped into a critical situation since they eat poisonous substances or drink strong acid. If the rescuers rush to perform mouth-to-mouth artificial respiration, they may suffer potential hazard to themselves. In view of the above situation, an artificial respiration mask is developed.

However, the existing artificial respiration mask has the following shortcomings in use: in the process of respiring the patient, the air flow may easily overflow from the patient's mouth, so the air cannot be completely imported into the patient, which seriously affects the quality of rescue; the air blown out by the rescuers and exhaled by the patients cannot be effectively filtered completely, which is easy to cause interactive infection, improve the risk of disease and reduce the willingness to rescue; in case of a need to move the patient's body or adjust the head, the mask is extremely easy to slip, which affects the efficiency of the rescue; moreover, in case of a wound on the patient's face (including the eye and the forehead), the blood, body fluids and mucous membranes cannot be effectively isolated, which may cause a big loophole to the protection.

BRIEF SUMMARY OF THE INVENTION

The first objective of the present invention is to provide a first-aid mask and an inflatable structure thereof, which makes use of a technical means to provide an air-sealed hood around the socket tube for sealing the air discharged from the pores between the socket tube and the mouth of the patient, so as to effectively import the air flow into the patient to significantly increase the survival rate of the patient.

The second objective of the present invention is to provide a first-aid mask and an inflatable structure thereof, which makes use of a technical means to connect a mask's body, so as to simultaneously filter the virus and bacteria blown out by the rescuers and the patients to prevent the mutual infection, with the aim to improve the willingness of the rescuers and the quality of the rescue.

The third objective of the present invention is to provide a first-aid mask and an inflatable structure thereof, which makes use of a technical means to attach a belt body set and a socket tube to the patient, so as to prevent the mask's body from offsetting or slipping in the process of rescue to avoid affecting the performance of the first aid, with the aim to improve the efficiency of the rescue.

To achieve the objectives above, the present invention adopts the following technical solution:

an inflatable structure which is provided in a mask's body, characterized in that the inflatable structure comprises:

a ventilation seat;

a sleeving connection which is sleeved at one end of the ventilation seat and sandwiches the mask's body together with the ventilation seat, wherein the sleeving connection has a socket tube, with the mask's body, the ventilation seat and the socket tube in air communication; and an air-sealed hood which is connected to the sleeving connection and provided around the socket tube.

The inflatable structure, characterized in that the sleeving connection has a sleeve, with one end of the sleeve sleeved on the ventilation seat and the other end connected to the socket tube.

The inflatable structure, characterized in that the end face of the connection between the sleeve and the socket tube is provided with a plurality of air guiding grooves, with the air guiding grooves in air communication with the socket tube.

The inflatable structure, characterized in that the end face of the connection between the sleeve and the socket tube is provided with a plurality of air guiding grooves, with the air-sealed hood abutted and surrounding these pores.

The inflatable structure, characterized in that the air-sealed hood and the sleeving connection are integrally molded.

The inflatable structure, characterized in that the air-sealed hood is a silicone ring or a rubber ring with a thickness of 1 mm~5 mm.

The inflatable structure, characterized in that the inflatable structure further comprises an air guiding hood in air communication with the other end of the ventilation seat.

A first-aid mask, characterized in that it comprises:

a mask's body which is provided with an outer layer;

an inflatable structure as described above, wherein the socket tube is provided in the direction of the outer layer of the mask's body; and a belt body set which is connected to the mask's body.

The first-aid mask, characterized in that the outer layer is an anti-splash breathable cloth or a nano silver woven cloth or a combination of both.

The first-aid mask, characterized in that the first-aid mask further comprises a pair of reflexed flaps which extend from the side edge of the mask's body respectively and are reflexed to be fixed to the mask's body at both ends thereof.

The first-aid mask, characterized in that the first-aid mask further comprises an eye shield which is fixed to the outer layer and extends from the mask's body.

According to the above-mentioned technical solution, the beneficial effects of the present utility model are as below:

(1) by virtue of the technology of connection of the air guiding hood onto the ventilation seat, the air flow blown out by the rescuers upon mouth-to-mouth contact can be intensively imported completely through the air guiding hood, so as to prevent the air flow probably flowing out from the gap between the mouth and the ventilation seat for a full and effective use of the imported air;

(2) by virtue of the design of the reflexed flaps extending from the side edge of the mask's body, the mask can fit the patient's face completely upon wearing to prevent the air flow flowing out from the gap between the mask and the face, so as to reduce the risks of infecting the surrounding people, while blocking the entry of external pollutants to improve the quality of the rescue;

(3) by virtue of the technology of the mask's body and the fixed eye shield, the blood, body fluids, mucous membranes and wounds of the patients or/and rescuers can be effectively isolated to prevent a cross-infection contact, so as to achieve a comprehensive protection for a relatively health and safe rescue;

(4) by making use of the mask's body, the mouths of the rescuers and the patients can be effectively prevented from direct contact, so as to avoid the patients from feeling that they are inadvertently violated and reduce the embarrassment of both parties after the patients wake up;

(5) by virtue of the design of an anti-splash breathable cloth or a nano silver woven cloth or a combination of both adopted for the outer layer of the mask's body, the present invention can realize the effective extermination of virus and bacteria, in addition to reducing the hot feeling of prolonged rescue and making it more comfortable to wear.

In the figures: 10—mask's body, 11—outer layer, 13—inner layer, 15—reflexed flaps, 20—inflatable structure, 21—ventilation seat, 211—through pore, 213—hook, 215—convex ring, 23—sleeving connection, 231—sleeve, 233—socket tube, 234—tube pore, 235—socket, 237—slot, 238—air guiding groove, 239—pore, 25—air-sealed hood, 27—air guiding hood, 30—belt body set, 31—belt, 40—eye shield, 5—the rescuer, 6—the patient, 7—N95-type mask, 71—elastic belt.

DETAILED DESCRIPTION OF THE INVENTION

The structure and features of the present invention will be described in detail by way of the following examples with reference to the accompanying drawings.

Figure 1:
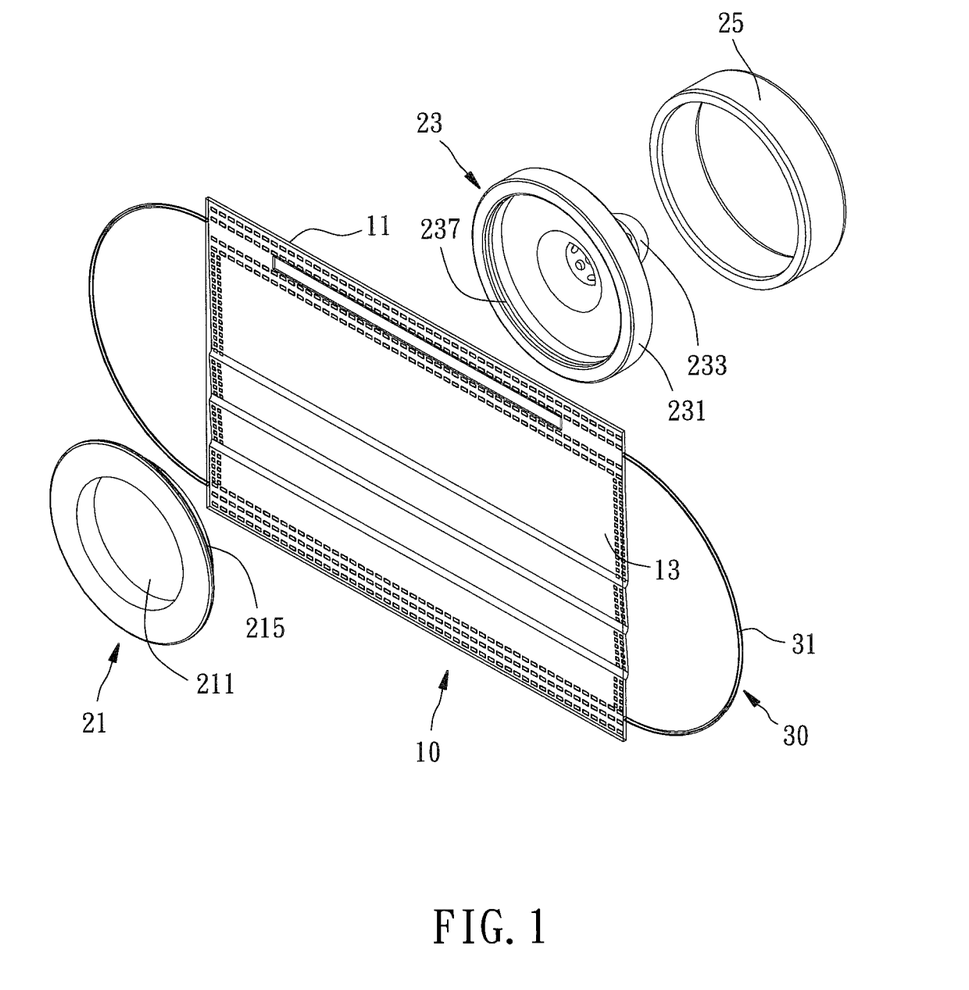
FIG. 1 is a perspective exploded view of the first-aid mask in the present invention.
Figure 2:
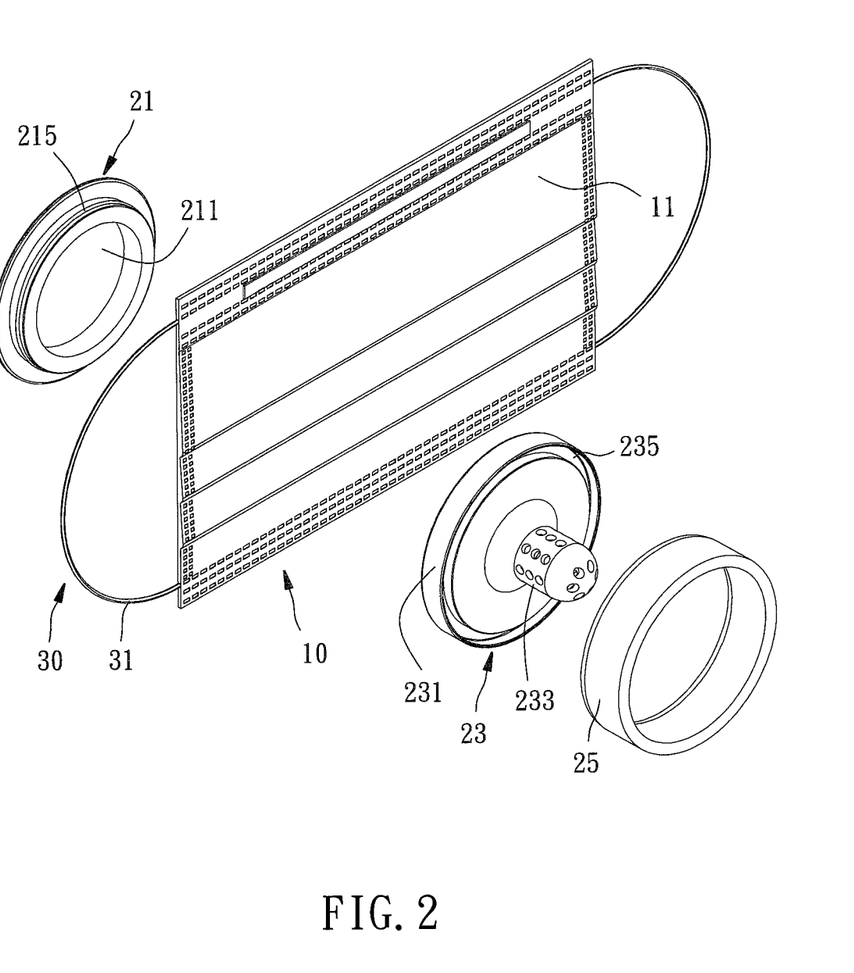
FIG. 2 is another view of FIG. 1.
Figure 3:
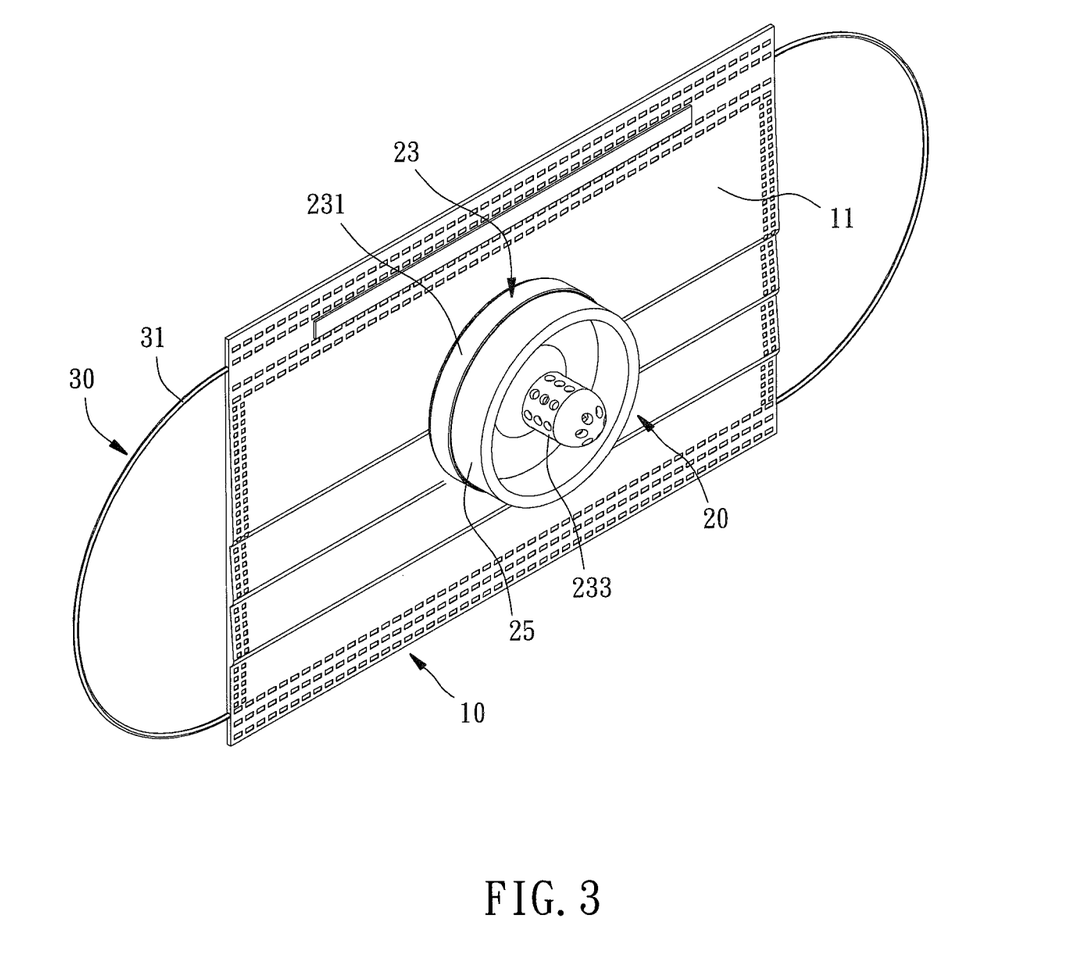
FIG. 3 is a perspective view of the assembly of the first-aid mask in the present invention.

Referring to FIG. 1 to FIG. 3, the present invention of a first-aid mask comprises a mask's body 10, an inflatable structure 20 and a belt body set 30 which will be described in details as follows:

the mask's body 11 is provided with an outer layer 11, an intermediate layer (not shown) and an inner layer 13, wherein the outer layer 11 may be an anti-splash cloth, a nano silver woven cloth or a non-woven cloth with high acid and alkali resistance or a combination of any of them, the intermediate layer may be filter cotton or active carbon fiber and the inner layer 13 may be a hydrophilic layer or a moisture absorbent cloth; the mask's body 100 may be a mask in which a fragrant essential oil or a herbal ingredient or a combination of both is added.

The inflatable structure 20 comprises a ventilation seat 21, a sleeving connection 23 and an air-sealed hood 25:

wherein a through pore 211 is formed in the center of the ventilation seat 21 and a convex ring 215 is formed on the outer periphery thereof, with the through pore 211 of a circular shape, an oval shape or a shape that can be aligned with the mouth shape;

wherein the sleeving connection 23 is sleeved at one end of the ventilation seat 21 and sandwiches the mask's body 10 together with the ventilation seat 21, with the sleeving connection 23 provided with a socket tube 233 so that the mask's body 10, the ventilation seat 21 and the socket tube 233 are in air communication; the sleeving connection 23 comprises a sleeve 231, a socket tube 233 connected to the sleeve 231 and a slot 237 which is formed in the inner wall of the sleeve 231 (as shown in FIG. 1) and can be positioned corresponding to the convex ring 215 of the ventilation seat 21, wherein the socket tube 233 is provided in the direction of the outer layer 11, serving to prop up the teeth in the mouth of the patient 6 and smooth the air transmission;

wherein the air-sealed hood 25, which is connected to the sleeving connection 23 and provided around the socket tube 233, may be a rubber ring or a silicone ring.

The belt body set 30, which is connected to the mask's body 10, comprises two belts 31 which are fixed to both sides of the mask's body 10 respectively, wherein the belts may be an elastic ear belt, a head-on elastic belt or a band.

Figure 4:
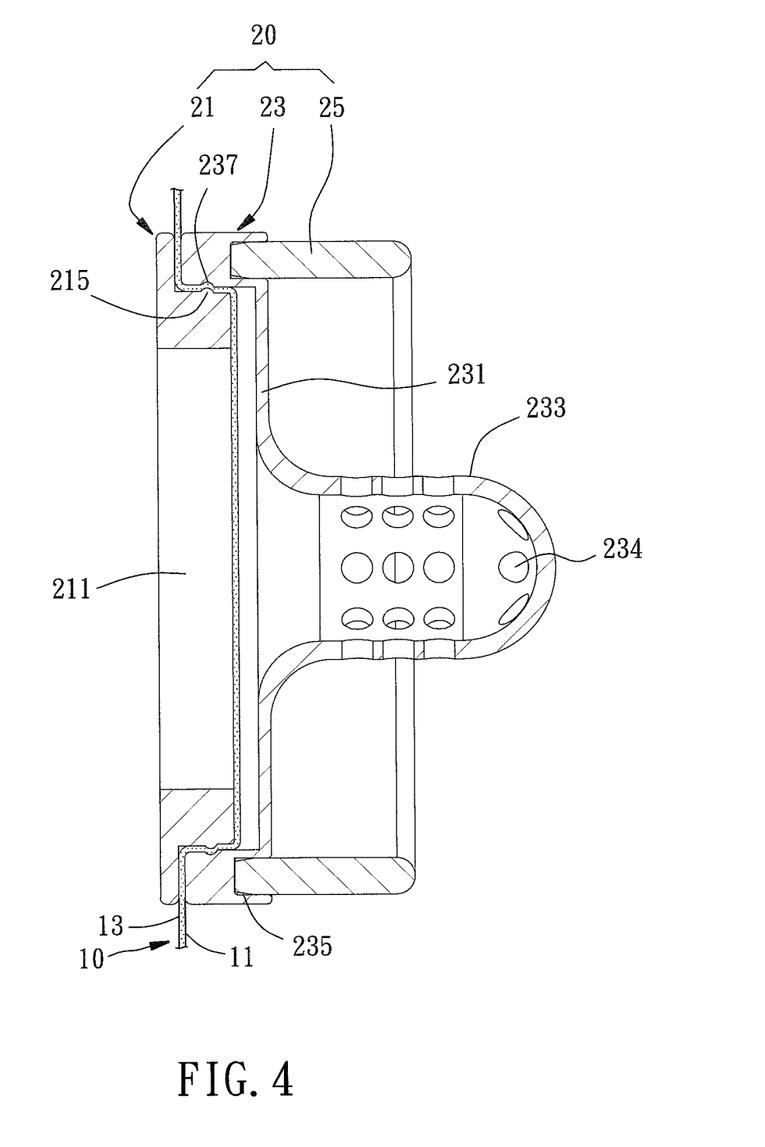
FIG. 4 is a cross-sectional view of the inflatable structure in FIG. 3.

Referring to FIG. 4, the present invention provides an inflatable structure 20 which is provided in a mask's body 10, characterized in that the inflatable structure 20 comprises a ventilation seat 21, a sleeving connection 23 and an air-sealed hood 25 which will be described in details as follows:

a through pore 211 is formed in the center of the ventilation seat 21 and a convex ring 215 is formed on the outer periphery thereof, with the through pore 211 of a circular shape, an oval shape or a shape that can be aligned with the mouth shape; alternatively, a ventilation seat 21, which is connected via standard ventilation, is used for connecting the oxygen supply system.

The sleeving connection 23 is sleeved at one end of the ventilation seat 21 and sandwiches the mask's body 10 together with the ventilation seat 21, with the sleeving connection 23 provided with a socket tube 233 so that the mask's body 10, the ventilation seat 21 and the socket tube 233 are in air communication; the sleeving connection 23 comprises a sleeve 231, a socket tube 233 connected to the sleeve 231 and a slot 237 which is formed in the inner wall of the sleeve 231 and can be positioned corresponding to the convex ring 215 of the ventilation seat 21: the socket tube 233 comprises at least one tube pore 234, serving to prop up the teeth in the mouth of the patient 6 and smooth the air transmission; preferably, the outer diameter of the socket tube 233 is 8 mm~16 mm.

The air-sealed hood 25 is connected to the sleeving connection 23 and provided around the socket tube 233, with specific methods of connection as follows: one end of the air-sealed hood 25 is inserted into the socket 235 of the sleeve 231 or the air-sealed hood 25 and the sleeving connection 23 can be integrally molded, wherein the air-sealed hood 25 with an outer diameter of 40 mm~60 mm and a thickness of 1 mm~5 mm may be a rubber ring or a silicone ring, and a medical-grade silica gel with an appropriate strength can be used for providing a good support and a comfortable contact.

Figure 5:
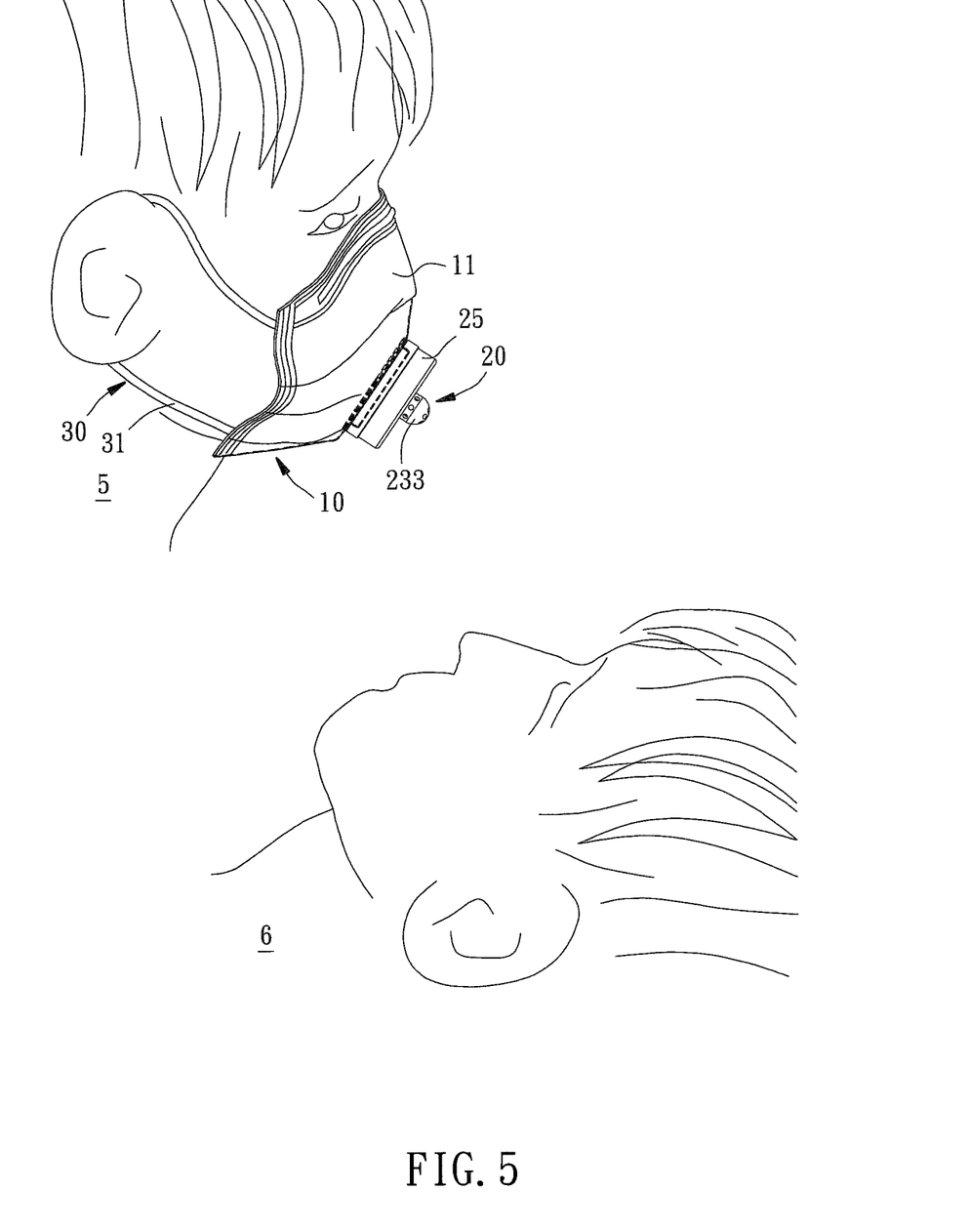
FIG. 5 is a schematic view of the first use state of the first-aid mask in the present invention.

In use of the present invention, as shown in FIG. 5, after putting on the present invention, the first-aid personnel or the rescuer 5 shall insert the socket tube 233 into the mouth of the patient 6, keeping the air-sealed hood 25 completely covering the mouth of the patient 6, and then pinch the nose of the patient 6 and blow out the air flow into the patient 6 to perform an mouth-to-mouth artificial respiration for a smooth rescue.

In the process of blowing out the air flow, the air flow can be completely and smoothly imported into the patient 6 upon an appropriate pressure of the air flow blown out by the rescuer, due to the better air permeability of the mask's body 10, so that the volume of the air flown into the patient 6 will not be insufficient.

As described above, an air-sealed hood 25 is provided around the socket tube 233 for sealing the air discharged from the pores between the socket tube 233 and the mouth of the patient 6, so as to effectively import the air flow into the patient 6 to significantly increase the survival rate of the patient.

Meanwhile, the mask's body 10 can simultaneously filter the virus and bacteria blown out by the rescuer 5 and the patient 6 to prevent the mutual infection, so as to improve the willingness of the rescuer and the quality of the rescue.

By virtue of the design of an anti-splash breathable cloth or a nano silver woven cloth or a combination of both adopted for the outer layer 11 of the mask's body 10, the present invention can realize the effective extermination of virus and bacteria, in addition to reducing the hot feeling of prolonged rescue and making it more comfortable to wear.

Figure 6:
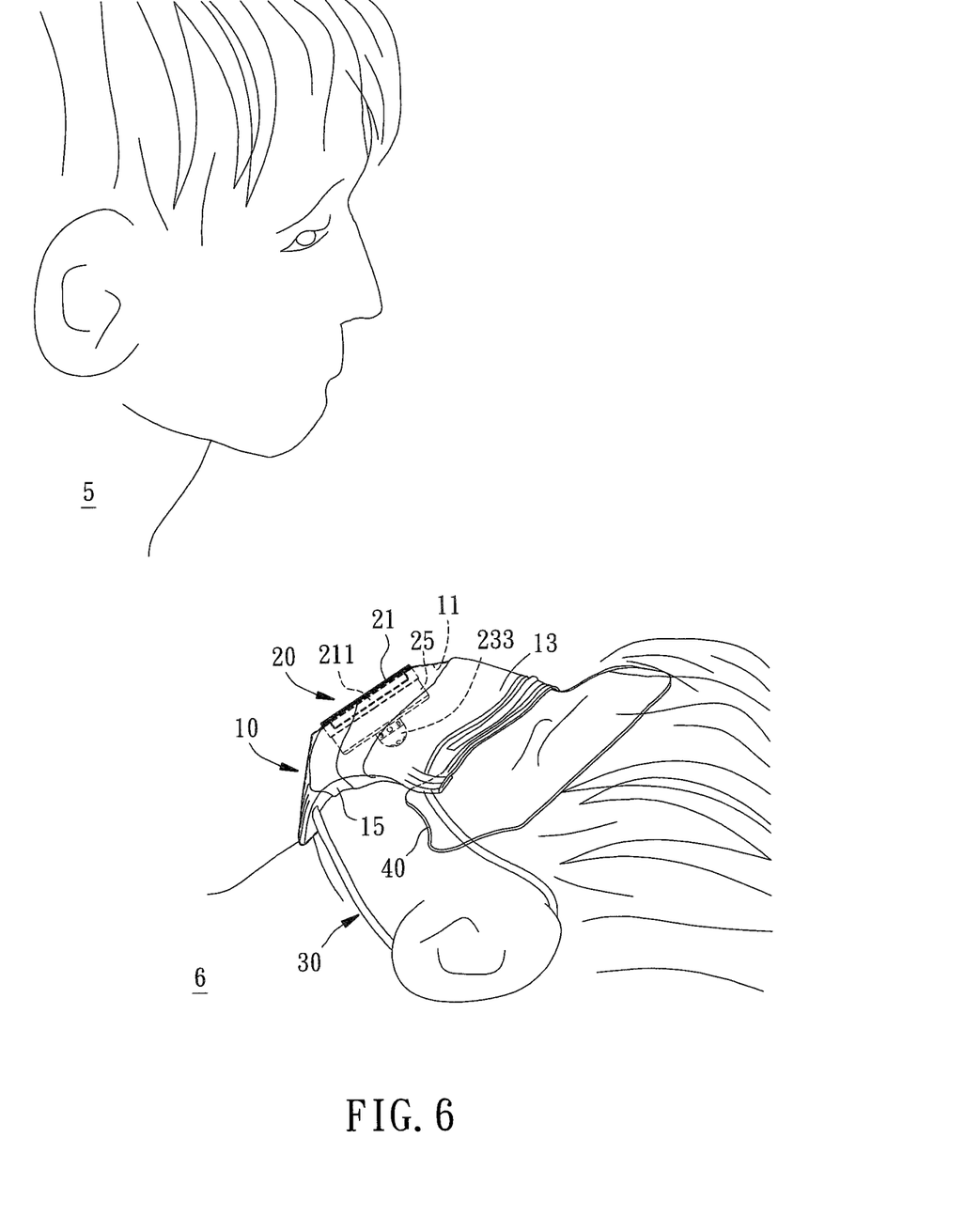
FIG. 6 is a schematic view of the second use state of the first-aid mask in the present invention.

In use of another embodiment of the present invention, as shown in FIG. 6, the present invention can be worn on the patient 6 and the socket tube 233 shall be inserted into the mouth of the patient 6, so that the air-sealed hood 25 completely covers the mouth of the patient 6, with the flaps on the bridge of the nose appropriately adjusted and closely pressed, and then the rescuer 5 shall pinch the nose of the patient 6 with the hand and use the mouth to communicate with the through hole 211 of the ventilation seat 21 to make the patient 6 exhale the air flow, so as to perform an mouth-to-mouth respiration for a smooth rescue, thus achieving the aforementioned results.

By virtue of a technical means to attach a belt body set 30 and a socket tube 233 to the patient 6, the mask's body can be prevented from offsetting or slipping in the process of rescue to avoid affecting the performance of the first aid, so as to improve the efficiency of the rescue.

The above-mentioned embodiment may further comprise a pair of reflexed flaps 15 which extend from the side edge of the mask's body 10 respectively and are reflexed to be fixed to the mask's body 10 at both ends thereof. By virtue of the design of the reflexed flaps 15, the mask can fit the face of the patient 6 completely upon wearing to prevent the air flow flowing out from the gap between the mask's body 10 and the face, so as to reduce the risks of infecting the surrounding people, while blocking the entry of external pollutants to improve the quality of the rescue.

The above-mentioned embodiment may further comprise an eye shield 40 fixed to the outer layer 11 and extends from the mask's body 10 which is waterproof, acid and alkali resistant and corrosion-resistant. By virtue of the technology of the mask's body 10 and the fixed eye shield 40, the blood, body fluids, mucous membranes and wounds of the rescuer 5 or/and the patient 6 (including eyes and foreheads) can be effectively isolated to prevent a cross-infection contact, so as to achieve a comprehensive protection for a relatively health and safe rescue.

Additionally, in addition to the patient's 6 wearing of the present invention, the rescuer 5 can wear a mask (not shown) to inflate the patient 6 for a rescue, which is protected by more layers to further enhance the protective effect.

Figure 7:
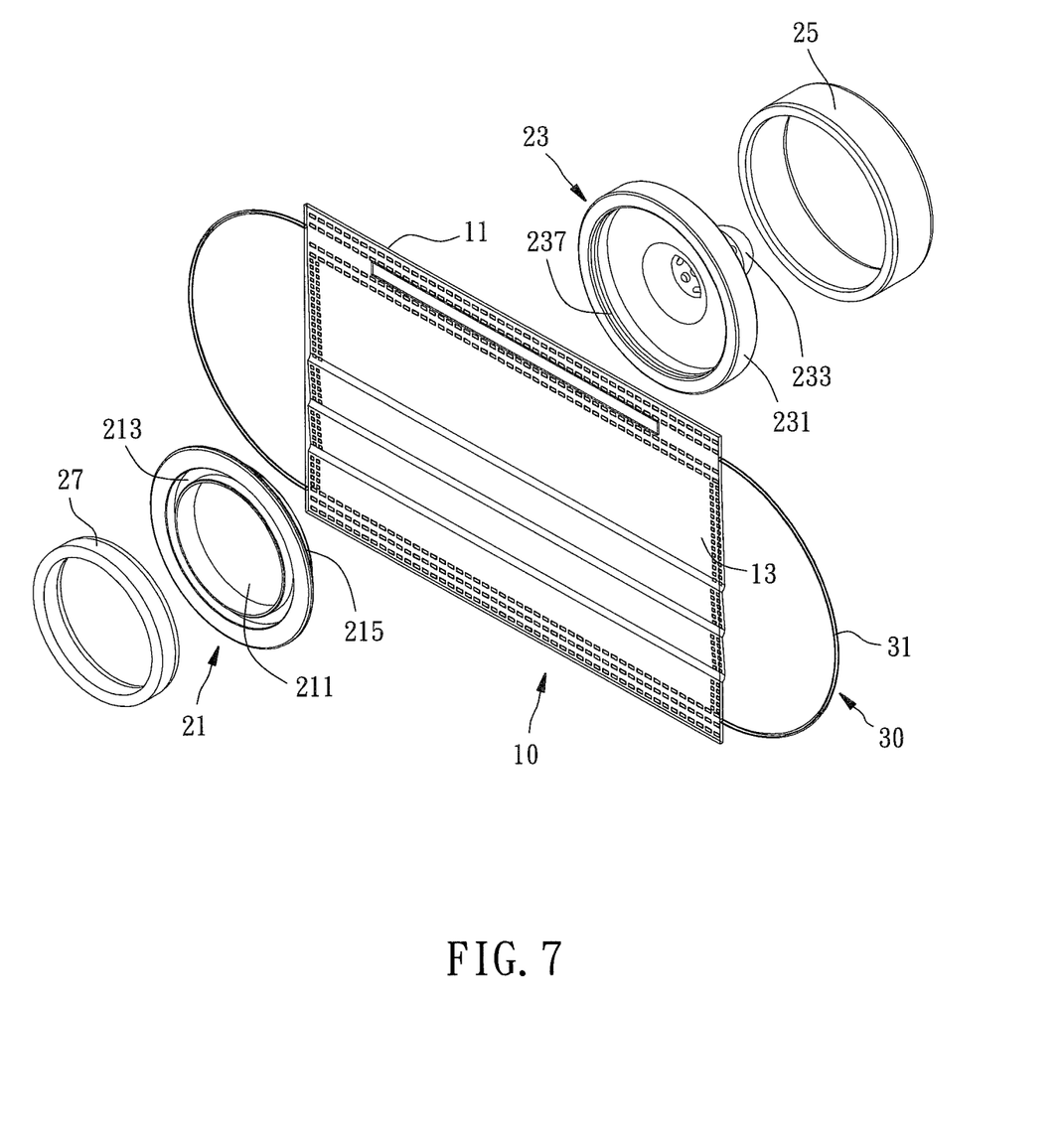
FIG. 7 is an exploded view of another embodiment of the first-aid mask in the present invention.
Figure 8:
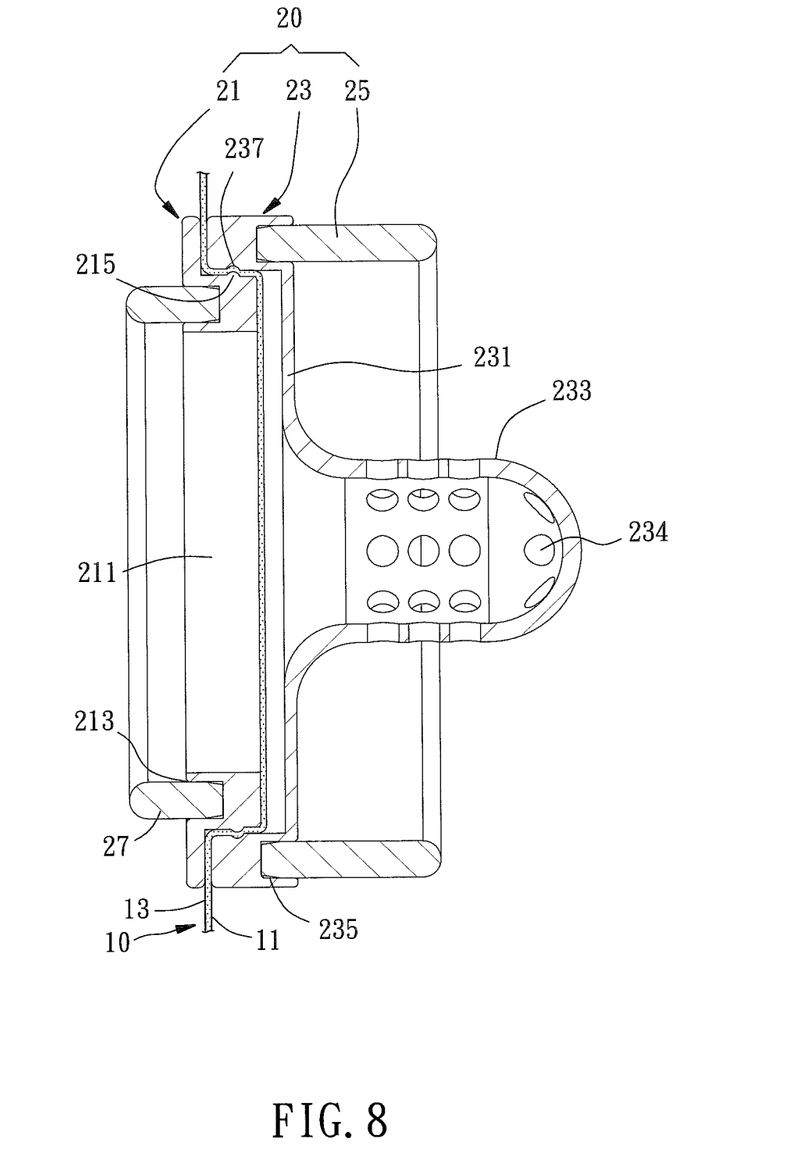
FIG. 8 is a cross-sectional view of the assembly of the structure in FIG. 7.

Referring to FIG. 7 and FIG. 8, another preferred embodiment of the present invention is provided, mainly in the same manner as in the prior art, with the differences as follows:

the embodiment may comprise an air guiding hood 27 connected to the other end of the ventilation seat 21. The air guiding hood 27 may be a rubber ring, a silicone ring or a sleeve, wherein the silicone ring may preferably be of a medical-grade silicone and the sleeve may be connected to the oxygen supply device.

The ventilation seat 21 has a through pore 211 and a groove 213 provided around the through pore 211, while one end of the air guiding hood 27 is inserted into the groove 213 or the air guiding hood 27 and the ventilation seat 21 are integrally formed.

By virtue of the technology of connection of the air guiding hood 27 onto the ventilation seat 21, the air flow blown out by the rescuer 5 upon mouth-to-mouth contact can be intensively imported completely through the air guiding hood 27, so as to prevent the air flow probably flowing out from the gap between the mouth and the ventilation seat 21 for a full and effective use of the imported air.

Figure 9:
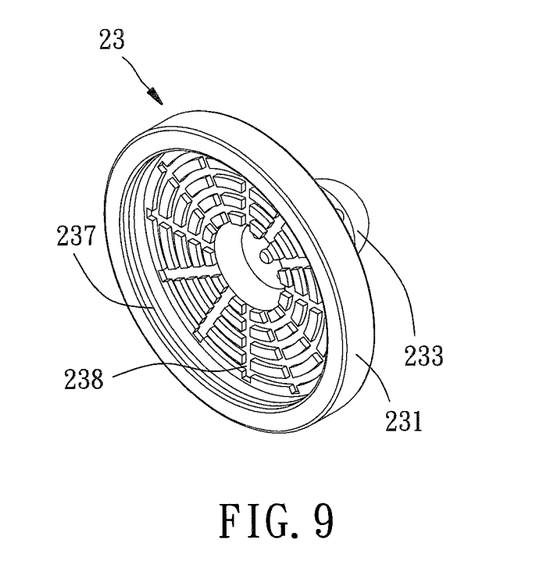
FIG. 9 is a schematic view of another embodiment of the inflatable structure in the present invention.

Referring to FIG. 9, another preferred embodiment of the present invention is provided, mainly in the same manner as in the prior art, with the differences as follows:

the end face of the connection between the sleeve 23 and the socket tube 233 of the sleeving connection 23 is provided with a plurality of air guiding grooves 238 which are in air communication with the socket tube 233, so that in the process of air transmission, the air flow can be intensively imported into the socket tube 233 via these air guiding grooves 238, so as to be imported into the patient 6 to achieve the aforementioned results.

Figure 10:
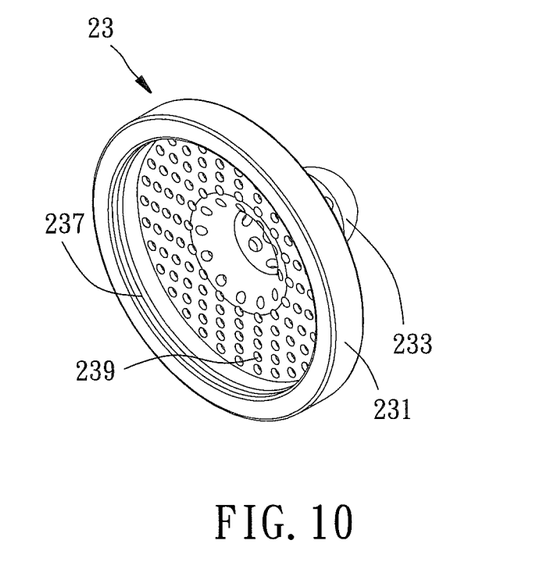
FIG. 10 is a schematic view of a further embodiment of the inflatable structure in the present invention.

Referring to FIG. 10, a further preferred embodiment of the present invention is provided, mainly in the same manner as in the prior art, with the differences as follows:

the end face of the connection between the sleeve 231 and the socket tube 233 of the sleeving connection 23 is provided with a plurality of through pores 239, with the air-sealed hood 25 abutted and surrounding these pores 239; in addition to the air transmission via the socket tube 233, the air flow can be imported into the patient 6 via these pores 239 from the pores between the socket tube 233 and the mouth of the patient 6 to achieve the aforementioned results.

Figure 11:
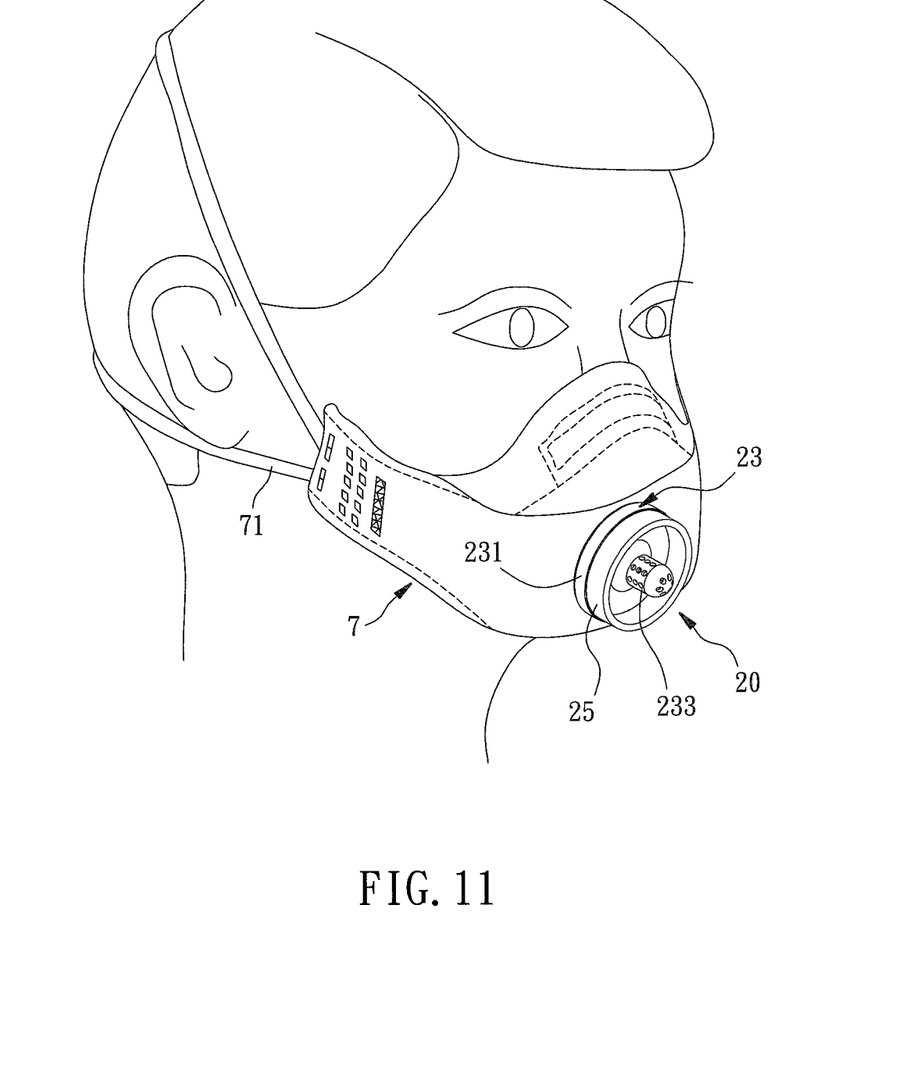
FIG. 11 is a schematic view of a further embodiment of the first-aid mask in the present invention.

Referring to FIG. 11, a further preferred embodiment of the present invention is provided, mainly in the same manner as in the prior art, with the differences are as follows:

the inflatable structure 20 in the present invention may be applied or installed into a N95-type mask 7 which is provided with two highly tensive head-mounted elastic belts 71 to increase the tightness and attachment of the mask 7 and the face.

Notably, the mouths of the rescuers and the patients can be effectively prevented from direct contact in the present invention, so as to avoid the patients 6 from feeling that they are inadvertently violated and reduce the embarrassment of both parties after the patients 6 wake up.

In view of the foregoing, the present invention has the following effects compared with the prior art: the present invention is comfortable to wear and permeable, the air flow can be more completely and effectively imported into the patient to significantly increase the survival rate of the patient, and meanwhile the mutual infection can be prevented to improve the willingness of the rescuers and the quality of the rescue, so that the efficiency of rescue is improved to better achieve a comprehensively protective effect.

Finally, it shall be further stated that those skilled in the art having the knowledge of the present invention should be expressly aware that the detailed description and the embodiments recited in the present invention are intended only to illustrate the efficacy of the structure of the invention, but not to limit the scope of the claims of the present invention, and substitutions or variations of other equivalents, components, objects, structures or devices should also be embraced by the claims of the invention.

INDUSTRIAL APPLICABILITY

The first-aid mask and the inflatable structure thereof disclosed in the invention have a wide prospect in clinical application, therefore having an expansive industrial applicability.

What is claimed is:

1. An inflatable structure which is provided in a mask's body, characterized in that the inflatable structure comprises:
   a ventilation seat;
   a sleeving connection which is sleeved at one end of the ventilation seat and sandwiches the mask's body together with the ventilation seat, wherein the sleeving connection has a socket tube, with the mask's body, the ventilation seat and the socket tube in air communication; and
   an air-sealed hood which is connected to the sleeving connection and provided around the socket tube,
   wherein the socket tube has a top end higher than a top end of the air-sealed hood, and
   wherein the socket tube is provided at the too end thereof with a plurality of tube pores.

2. The inflatable structure as claimed in claim 1, wherein the sleeving connection has a sleeve, with one end of the sleeve sleeved on the ventilation seat and the other end connected to the socket tube.

3. The inflatable structure as claimed in claim 2, wherein an end face of the connection between the sleeve and the socket tube is provided with a plurality of air guiding grooves, with the air guiding grooves in air communication with the socket tube.

4. The inflatable structure as claimed in claim 2, wherein an end face of the connection between the sleeve and the socket tube is provided with a plurality of through pores, with the air-sealed hood abutted and surrounding the through pores.

5. A first-aid mask, comprising:
   a mask's body which is provided with an outer layer;
   an inflatable structure as claimed in claim 1, wherein the socket tube is provided in the direction of the outer layer of the mask's body; and
   a belt body set which is connected to the mask's body.

6. The first-aid mask as claimed in claim 5, wherein the outer layer is an anti-splash breathable cloth or a nano silver woven cloth or a combination of both.

7. The first-aid mask as claimed in claim 5, further comprising a pair of reflexed flaps which extend from the side edge of the mask's body respectively and are reflexed to be fixed to the mask's body at both ends thereof.

8. The first-aid mask as claimed in claim 5, further comprising an eye shield which is fixed to the outer layer and extends from the mask's body.

9. The inflatable structure as claimed in claim 1, wherein the air-sealed hood and the sleeving connection are integrally molded.

10. The inflatable structure as claimed in claim 1, wherein the air-sealed hood is a silicone ring or a rubber ring with a thickness of 1 mm-5 mm.

11. The inflatable structure as claimed in claim 1, further comprising an air guiding hood in air communication with the other end of the ventilation seat.

\* \* \* \* \*